(12) United States Patent
Sager et al.

(10) Patent No.: US 6,518,747 B2
(45) Date of Patent: Feb. 11, 2003

(54) METHOD AND APPARATUS FOR QUANTITATIVE DETERMINATION OF ACCUMULATIONS OF MAGNETIC PARTICLES

(75) Inventors: Ronald E. Sager, Carlsbad, CA (US); Michael B. Simmonds, Mammoth Lakes, CA (US); Jost H. Diederichs, Poway, CA (US); Kurt G. Jensen, Poway, CA (US); Randall C. Black, San Diego, CA (US)

(73) Assignee: Quantum Design, Inc., San Diego, CA (US)

( * ) Notice: Subject to any disclaimer, the term of this patent is extended or adjusted under 35 U.S.C. 154(b) by 55 days.

(21) Appl. No.: 09/785,403

(22) Filed: Feb. 16, 2001

(65) Prior Publication Data

US 2002/0135358 A1 Sep. 26, 2002

(51) Int. Cl.$^7$ .................. G01N 27/74; G01N 15/06; G01N 33/553
(52) U.S. Cl. .................. 324/204; 324/71.4; 324/235; 422/68.1; 436/526
(58) Field of Search .................. 324/204, 214–217, 324/226, 228, 235, 251, 252, 71.1, 71.4; 209/546, 547, 567–570; 422/68.1; 436/526

(56) References Cited

U.S. PATENT DOCUMENTS

| | | | |
|---|---|---|---|
| 3,195,043 A | * | 7/1965 | Burig et al. .................. 324/235 |
| 3,342,991 A | * | 9/1967 | Kronenberger .......... 324/251 X |
| 4,037,150 A | * | 7/1977 | Taranov et al. .............. 324/251 |
| 4,518,919 A | * | 5/1985 | Ishida ..................... 324/235 X |
| 4,537,861 A | | 8/1985 | Elings et al. |
| 4,677,910 A | * | 7/1987 | Kuhfuss .................. 209/569 X |
| 4,810,963 A | | 3/1989 | Blake-Coleman et al. |
| 4,876,504 A | | 10/1989 | Blake et al. |
| 4,913,863 A | | 4/1990 | Imai et al. |
| 5,001,424 A | | 3/1991 | Kellett et al. |
| 5,034,689 A | | 7/1991 | Inoue et al. |
| 5,158,895 A | | 10/1992 | Ashihara et al. |
| 5,290,708 A | | 3/1994 | Ashihara et al. |
| 5,318,914 A | | 6/1994 | Matte et al. |
| 5,445,970 A | | 8/1995 | Rohr |
| 5,445,971 A | | 8/1995 | Rohr |
| 5,457,382 A | * | 10/1995 | Stein ....................... 324/262 X |
| 5,482,839 A | | 1/1996 | Ashihara et al. |
| 5,486,457 A | | 1/1996 | Butler et al. |
| 5,512,822 A | * | 4/1996 | Masuda ....................... 324/235 |
| 5,558,839 A | | 9/1996 | Matte et al. |
| 6,046,585 A | | 4/2000 | Simmonds |
| 6,310,475 B1 | * | 10/2001 | Kawase et al. .............. 324/235 |

FOREIGN PATENT DOCUMENTS

| | | |
|---|---|---|
| EP | 0625708 | 11/1994 |
| GB | 2207510 | 2/1989 |
| JP | 6390765 | 4/1988 |
| WO | WO 96/10644 | 4/1996 |

OTHER PUBLICATIONS

D.R. Baselt et al, A Biosensor Based on Force Microscope Technology, Naval Research Laboratory, J. Vac. Science Tech. B., vol. 14, No. 2 (5 pp) (4/96).

* cited by examiner

Primary Examiner—Gerard R. Strecker
(74) Attorney, Agent, or Firm—The Maxham Firm

(57) ABSTRACT

Apparatus for detection and measurement of agglutinations of magnetic particles employing Hall sensors. A low frequency AC signal is employed to excite or bias the Hall sensors which reside in a DC magnetic field. The particles are moved into operative relationship with the Hall sensors in order to generate a signal representing the number of particles on the substrate. The method for such detection and measurement is also part of the invention.

53 Claims, 4 Drawing Sheets

METHOD AND APPARATUS FOR QUANTITATIVE DETERMINATION OF ACCUMULATIONS OF MAGNETIC PARTICLES

BACKGROUND OF THE INVENTION

1. Field of the Invention

This invention relates generally to sensing the presence of magnetic particles, and more particularly to quantitatively measuring accumulations of such particles by means of DC magnetic excitation and sensing of the amplitude of the resulting excitation of the magnetic moments of the particles.

2. Discussion of Related Art

Much attention has been given to techniques for determining the presence, and possibly the level of concentration, of minute particles in a larger mixture or solution in which the particles reside. It is desirable in certain circumstances to measure very low concentrations of certain organic compounds. In medicine, for example, it is very useful to determine the concentration of a given kind of molecule, usually in solution, which either exists naturally in physiological fluids (for example, blood or urine) or which has been introduced into the living system (for example, drugs or contaminants).

One broad approach used to detect the presence of a particular compound of interest is the immunoassay technique, in which detection of a given molecular species, referred to generally as the ligand, is accomplished through the use of a second molecular species, often called the antiligand or the receptor, which specifically binds to the ligand of interest. The presence of the ligand of interest is detected by measuring, or inferring, either directly or indirectly, the extent of binding of ligand to antiligand.

A good discussion of several detection and measurement methods appears in U.S. Pat. 4,537,861 (Elings et al.). The patent is directed to several ways to accomplish homogenous immunoassays in a solution of a binding reaction between a ligand and an antiligand which are typically an antigen and an antibody. The teaching of Elings is to create a spatial pattern formed by a spatial array of separate regions of antiligand material attached to a solid substrate. The corresponding ligand, which has been previously labeled by attaching to it a molecule or particle which has a particular physical characteristic, is then dispersed over the solid substrate such that the labeled ligand can produce a binding reaction with the antiligand in the spatial patterns. After the labeled bound complexes have been accumulated in the spatial patterns, equipment is used to scan the solid substrate, thereby measuring the physical characteristic of the labels to provide the desired immunoassay. The scanner may be based on fluorescence, optical density, light scattering, color and reflectance, among others. In addition, Elings further teaches that the magnetic particles may also be attached to either the ligand or the labeled ligand for the purpose of accumulating the labeled bound complexes within the solution or onto the prepared substrate surface, after which the scanning techniques previously described are employed.

Indeed, magnetic particles made from magnetite and inert matrix material have long been used in the field of biochemistry. They range in size from a few nanometers up to a few microns in diameter and may contain from 15% to 100% magnetite. They are often described as superparamagnetic particles or, in the larger size range, as magnetic beads. The usual methodology is to coat the surface of the particles with some biologically active material which will cause them to bond strongly with specific microscopic objects or particles of interest (proteins, viruses, cells, DNA fragments, for example). The magnetic particles then become "handles" by which the objects can be moved or immobilized using a magnetic gradient, usually provided by a strong permanent magnet. The Elings patent is an example of this use of magnetic particles. Specially constructed fixtures using rare-earth magnets and iron pole pieces are commercially available for this purpose.

Although these magnetic particles have been used primarily for moving or immobilizing the bound objects, some experimental work has been done on using the particles as tags for detecting the presence of the bound complexes. Historically, the detection and quantification of the bound complexes has been accomplished by means of radioactive, fluorescent, or phosphorescent molecules which are bound to the complexes of interest. These prior tagging techniques have various important weaknesses. Radioactive methods present health and disposal problems of the resulting low-level radioactive waste, and they are also relatively slow. Fluorescent or phosphorescent techniques are limited in their quantitative accuracy and dynamic range because emitted photons may be absorbed by other materials in the sample (see Japanese patent publication 63-90765, published Apr. 21, 1988, Fujiwara et al.). Furthermore, the signal from the fluorescent or phosphorescent molecules normally decays over a period of hours or perhaps days, at the most.

On the other hand, since the signal from a tiny volume of magnetic particles is exceedingly small, it has been natural that researchers have tried building detectors based on Superconducting Quantum Interference Devices (SQUIDs), which are well known to be the most sensitive detectors of magnetic fields for many applications. There are several substantial difficulties with this approach, however. Since the pickup loops of the SQUID must be maintained at cryogenic temperatures, the sample must be cooled to obtain a very close coupling to these loops. This procedure makes the measurements unacceptably tedious, and is inappropriate for many biotechnology applications. In addition, the general complexity of SQUIDS and their associated cryogenic components renders them extremely expensive and generally unsuitable for use in an inexpensive desktop instrument. Even a design based on "high Tc" superconductors does not completely overcome these objections, and would introduce several new difficulties, as discussed in Fujiwara et al.

More traditional approaches to detecting and quantifying the magnetic particles have typically involved some form of force magnetometry, in which the sample is placed in a strong magnetic gradient and the resulting force on the sample is measured. In a force-balance magnetometer, for example, the force is measured as an apparent change in the weight of the sample as the gradient is changed. An example of this technique is shown in Rohr U.S. Pat. Nos. 5,445,970 and 5,445,971. A more sophisticated technique measures the effect of the particle on the deflection or vibration of a micromachined cantilever (see Baselt et al., *A Biosensor based on Force Microscope Technology*, Naval Research Lab., J. Vac. Science Tech. B., Vol 14, No. 2, 5pp, April 1996). These approaches are all limited in that they rely on converting an intrinsically magnetic effect into a mechanical response, which must then be distinguished from a large assortment of other mechanical effects such as vibration, viscosity, and buoyancy, which can substantially interfere with the intended measurement.

In U.S. Pat. No. 6,046,585, Simmonds describes a technique employing a small region (the "gap") in a toroidal magnetizer, within which one places a pair (or multiple pairs) of inductive detection coils and generates a high-frequency oscillating magnetic field (the "drive field"). In this implementation, the individual detection coils are carefully matched in size but counter-wound, so that in the absence of any other magnetic materials (such as magnetic particles which are part of magnetic bound complexes) the pair of coils produces a zero output voltage. In other words, the drive field couples exactly the same but with opposite polarity to each of the counter-wound coils, so that the voltages from the individual coils algebraically sum exactly to zero.

When an accumulation of magnetic particles on a solid substrate is placed in the gap in close proximity to the detection coils, the oscillating drive field produces a corresponding oscillating magnetization in the magnetic particles, which can then be detected by the detection coils. In the Simmonds patent, the physical size of the particle accumulations are closely matched to the size of one of the detection coils so that the accumulation of particles gives a signal in one coil at a time as the substrate is moved past the detection coil array. In this sense, one can think of the accumulation of magnetic particles as changing the effective balance of the detection coil array as the particle accumulation moves past the detection coils. As taught in Simmonds, the largest signal is obtained from any given accumulation of magnetic particles when the physical dimensions of the accumulation matches the dimensions of one of the individual coils in the detection coil array.

In the Simmonds implementation, the high frequency oscillating field (typically having a maximum amplitude of 500 to 1000 Oersted) serves two functions. First, it produces a large magnetization in the magnetic particles, and secondly, the high frequency nature of the oscillating field causes the induced magnetization of the magnetic particles to oscillate at the same frequency as the drive field (typically of order 100 KHz). Since the voltage induced in the inductive detection coils is proportional to the frequency of the detected signal, using a high frequency drive field with the inductive detection coils increases the sensitivity of the device and allows one to detect an extremely small quantity of magnetic particles.

A pending patent application related to the invention disclosed in Simmonds extends the basic concept in several ways (Ser. No. 09/451,660, filed Nov. 30, 1999, now U.S. Pat. No. 6,437,563 B1). First, it describes the use of an E-core design to provide higher symmetry in forming the gap, thereby allowing one to generate large drive fields while maintaining a high degree of balance with respect to the detection coils. Secondly, it discloses the use of alternative detection systems, including the use of other sensors such as fluxgate, giant magneto-resistance (GMR), colossal magneto-resistance (CMR), and Hall effect sensors, all still employing an AC drive field.

The detection system described by Simmonds exploits the fundamental magnetic behavior of the material comprising the magnetic particles to detect and measure their magnetization. The beads used in these applications are typically described as superparamagnetic, meaning that the beads are magnetic only when placed in an applied magnetic field. More specifically, they are not magnetic in the absence of an externally applied field, which is equivalent to saying that the beads have no (zero) remanent magnetization. In fact, beads used in biotechnology applications are rather carefully designed to have zero remanent magnetization because beads which do have a remanent magnetization stick together and clump up when placed in solution, causing a variety of problems. Hence, any device designed to detect or measure the magnetization of the beads typically used in biotechnology applications can work only if an external field is applied to the beads while the measurement is being performed. This situation should be distinguished from the techniques used in magnetic recording, where the magnetic film on the tape or disc is specifically designed to have a high remanent magnetization and a large coercive field. (The coercive field of a material gives the value of magnetic field that must be applied to completely demagnetize the material.) In fact, in recording applications the large remanent magnetization is the means by which information is actually stored.

The magnetic particles typically used in biotechnology applications are comprised of iron oxide, which is typically a mixture of $Fe_3O_4$ and $Fe_2O_3$, and measurements on particles from a variety of manufacturers have shown that the saturation magnetization of all these particles, regardless of their size, is about 500 Oersted. This is a very typical saturation field for these types of ferrite materials. To be more specific, this means that below about 500 Oersted, applying a larger field to the particles increases the magnetization of the particles, potentially increasing the signal to be detected. At fields above the saturation field, however, this effect is greatly reduced so that further increases in the applied magnetic field produce little or no increase in the magnetization of the particles. Furthermore, in virtually every magnetic detection system, noise sources exist that increase in proportion to the ambient magnetic field. Hence, increasing the applied field beyond the saturation level can actually degrade the measurement by decreasing its signal-to-noise ratio. The increase in the applied field can also make the undesired contribution to the signal from ferromagnetic contaminants more apparent. Hence, if one wishes to determine the number of particles present by measuring their magnetization, the optimal signal-to-noise ratio for such a measurement will normally be achieved by applying a magnetic field which is about the same as the saturation field of the particles—in our case about 500 Oersted.

As discussed above, the Simmonds patent describes a technique for making quantitative measurements of superparamagnetic particles in bound complexes by applying a large oscillating magnetic field to the particles and detecting the oscillating magnetization induced in the particles. In this implementation, the sensors must be of the type which function well in the presence of a large oscillating magnetic field. The Simmonds apparatus is extremely sensitive and works very well. However, there are several factors which add complexity to the Simmonds design. Most importantly, because the Simmonds detection system works at a high frequency (typically about 100 KHz), there are capacitive coupling effects between the sample/substrate combination and the detection coils. In addition, such high frequency systems are always subject to phase shifts between the applied AC drive field and the detected signal. These effects can be very large when operating such a detection system at 100 KHz, and must be precisely accounted for if the system is to make an accurate measurement of the magnetization of the particles. Furthermore, generating the high frequency AC drive field in the gap of the toroidal magnetizer requires a significant amount of power, producing the possibility of thermal drifts in the detection electronics, especially immediately after the unit is first energized. The high power requirements of the AC drive field also impose a limitation on the length of time during which any such system can operate when running on battery power. And finally, the AC drive in the magnet and coil can potentially generate RF emissions which must be guarded against.

SUMMARY OF THE INVENTION

Broadly speaking, the present invention provides a greatly simplified and inexpensive method and apparatus for directly sensing and measuring very small accumulations of magnetic particles (for example, magnetite) and consequently, the bound complexes of interest.

A central feature of this invention is the use of a DC magnetic field (which replaces the time varying drive field in the prior art) to induce a magnetization in the magnetic particles, combined with the use of Hall sensors to detect the induced magnetization. The advantages of using a DC field instead of a time varying field are significant.

Generating a DC magnetic field in the implementation of this invention requires no field generating power source, is much simpler to implement than the prior AC driven system in the prior art, and can reduce the cost of the components by about two orders of magnitude. The requisite DC magnetic field can be generated without power consumption by using inexpensive permanent magnets and one or more pieces of iron to provide the appropriate field profile. In an exemplary prototype, the components used to produce the DC magnetic field cost less than about 25 cents. In contrast, the components used to generate the high frequency AC field used in previous devices cost in excess of twenty dollars and require significant power.

The power requirement to generate the 100 KHz AC field also limits the volume of the measurement region (the gap) in the devices which use an AC drive field, because the power required to generate the field increases with the volume of the gap. Increasing the ratio of area to height of the gap improves the field uniformity in the gap, but in systems which use AC drive fields this carries the penalty of increased power consumption. Increasing the volume of the gap when using a DC magnetic field requires only that correspondingly larger permanent magnets be used. A prototype system achieved fields in the order of 1000 Oersted in gaps having more than twice the volume of the Simmonds AC system.

The rather large magnetic field required to optimize these measurements (of order 500 Oersted) is incompatible with some types of sensors. However, the sensitivity of Hall sensors is not substantially degraded in high fields. In fact, Hall sensors can be designed to perform optimally in fields of this magnitude. The sensor area should also be matched to the sample size to maximize measurement sensitivity. While other types of sensors, including GMR and CMR sensors, can be engineered to meet the above criteria, Hall sensors matching these criteria are readily available and inexpensive.

A typical Hall sensor that might be used in this type of implementation is biased with approximately 10 to 20 milliamps of current. The output voltage of the sensor is proportional to both the applied field and the bias current. Hence, variations in the bias current will produce corresponding variations in the output signal, and it can be difficult electronically to produce extremely stable DC currents. This problem can be easily addressed, however, by applying an AC current to the Hall sensors, typically at a few kilohertz, which allows the generation of very stable peak amplitudes. Biasing the Hall sensors in this fashion also allows the detection system to work at a few kilohertz, thereby taking advantage of phase detection techniques to greatly improve the achievable signal-to-noise levels. (However, it should be understood that an AC current is not required in this invention, in which case there is simply a more stringent demand on the stability of the electronic circuitry that supplies the bias current for the sensors.)

A detection system using a DC magnetic field will also be largely immune to capacitive effects between the sample and the Hall sensors. In the high-frequency AC system of Simmonds, the dielectric properties in the sample substrate can cause significant capacitive coupling between the inductive detection coils, producing spurious signals. While these can be rejected using appropriate phase detection schemes, the DC system using Hall sensors is highly resistant to AC-coupled capacitive effects.

In the preferred embodiment, two individual Hall effect sensors are placed next to each other in an applied magnetic field, to form a matched pair of sensors. Each sensor produces a signal indicative of the magnetic field detected by the sensor. The signal from one sensor is subtracted from the other to form a resultant signal indicative of the difference in magnetic field in one sensor versus the signal in the other sensor. Performing this subtraction of signals electronically will significantly attenuate the unwanted resultant signal due to the applied field. Such a configuration of sensors is known as a "gradiometer" in the magnetic sensing industry.

In practice the measurement is performed by moving a well-defined pattern of magnetically susceptible particles past the two Hall sensors and in close proximity to them, while the particles are simultaneously exposed to the DC magnetic field. As taught in the Simmonds prior art, it is important to have the spatial dimensions of the pattern of magnetic particles closely match the physical dimensions of the Hall sensor. In this case, the pattern of magnetic particles is detected by the first Hall sensor as it moves past, and then after leaving the detection area of the first sensor, it is subsequently detected by the second Hall sensor. Since the two Hall sensors are connected such that they produce signals of opposite polarity, the difference signal between the two sensors is a function of the position of the spatial pattern as it moves past the two sensors, thereby indicating the number of particles present.

BRIEF DESCRIPTION OF THE DRAWING

The objects, features and advantages of the invention will be more clearly perceived from the following detailed description, when read in conjunction with the accompanying drawing, in which.

DETAILED DESCRIPTION OF THE PREFERRED EMBODIMENTS

Figure 1:
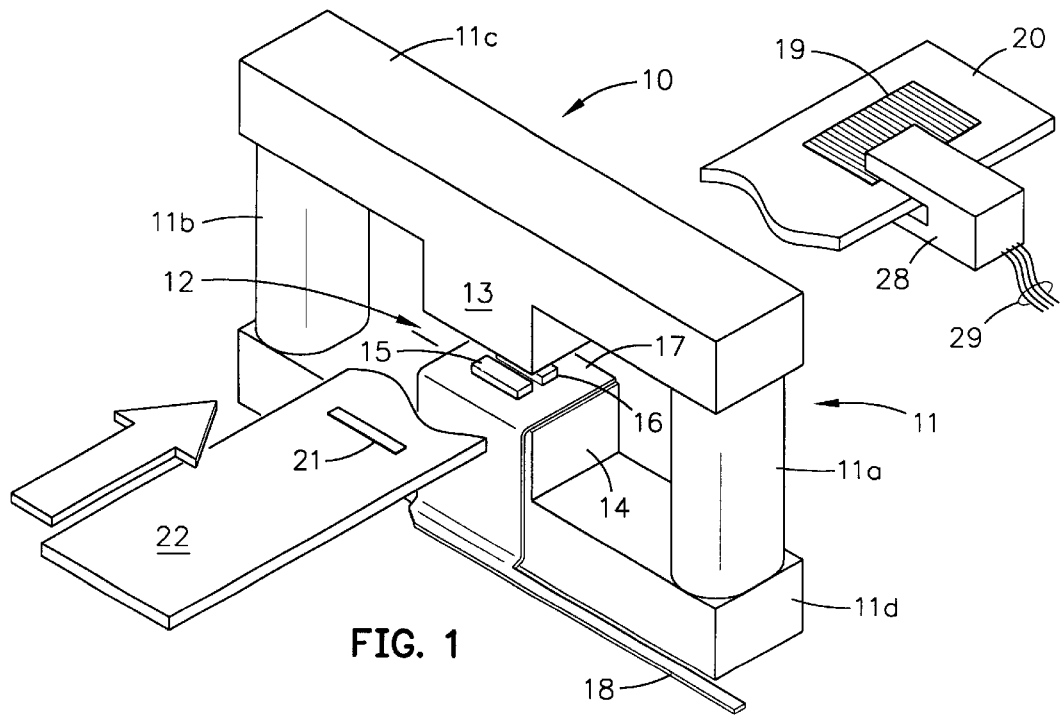
FIG. 1 is a perspective representation of a preferred embodiment of the apparatus of this invention.

With reference now to the drawing, and more particularly to FIG. 1, there is shown an apparatus 10 configured in accordance with the present invention. Permanent magnet structure 11 is shown as having an E configuration, with gap 12 formed between middle leg segments 13 and 14. The magnet is comprised of magnet elements 11A and 11B and iron pole pieces 11C and 11D. Hall sensors 15 and 16 are mounted on surface 17, which is contemplated to be a flexible printed circuit board providing all the external connections required between the Hall sensors and circuitry to which they are connected by means of the leads in tail 18.

Sample 21 is placed in a defined pattern (generally 1 mm ×2 mm) on substrate 22 and is moved into gap 12 past Hall sensors 15 and 16 to provide output signals from the FIG. 4 circuitry, for example, as discussed in detail below. Further details of this motion and the sensor outputs will be set out later in discussing FIGS. 7 and 8.

As an alternative improvement, substrate 22 may be formed with extension 20 on which is printed bar code 19. The bar code is read by optical detector or bar code reader 28, shown with appropriate electrical leads 29. The bar code is spaced from sample pattern 21 by a predetermined distance and reader 28 has a fixed position with respect to the Hall sensors. The signals from the reader can then provide information about the position of the sample pattern with respect to the Hall sensors.

As contemplated, the optical detector is a fairly sophisticated commercial device which issues two pulses each time one of the bar code lines passes through the detector. The first pulse is corresponds to the leading edge of the bar coded line, and the second pulse (in quadrature) corresponds to the trailing edge of the bar coded line. In this implementation, these pulses are used to trigger the data collection electronics which measures and stores the voltage output of the two Hall sensors, and these pulses are also used to control the current reversal when an AC current is used to bias the Hall sensors. In a similar manner, the pulses from the optical detector (or perhaps a second optical detector) can be used to initiate and terminate the data collection process. Hence, the bar code information can tell the electronic control system when to start and stop the data collection, as well as provide the position information for each measurement of the signal from the Hall sensors as the sample moves past.

Figure 2:
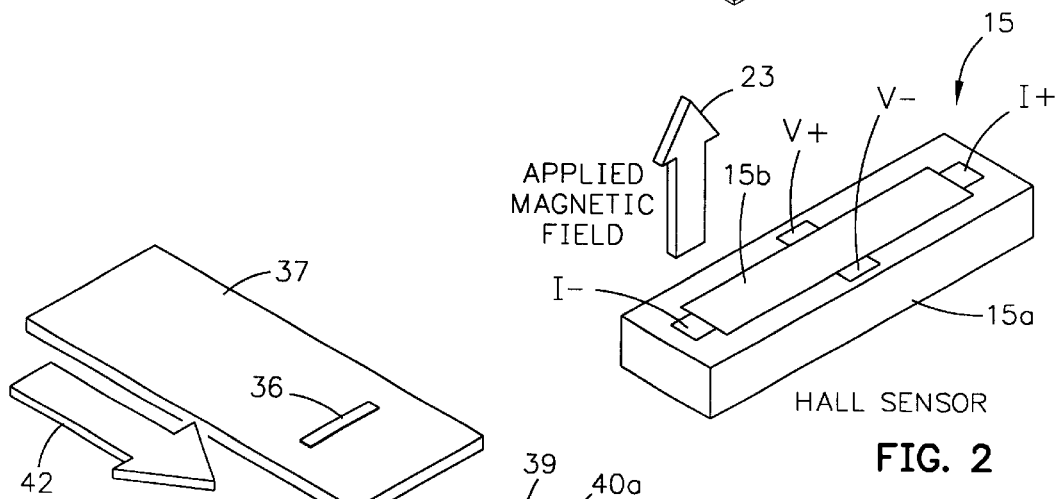
FIG. 2 shows a Hall sensor as employed in the FIG. 1 embodiment.

The principal of operation of a Hall sensor is shown in FIG. 2. Low frequency AC is applied at I+ and I− to bias or excite Hall sensor 15, the sensitive area 15B of which is on substrate 15A. Output voltages V+ and V− are applied to the FIGS. 4 and 5 circuitry as will be explained in greater detail below. The applied magnetic field from magnet 11 is represented by arrow 23.

Figure 4:
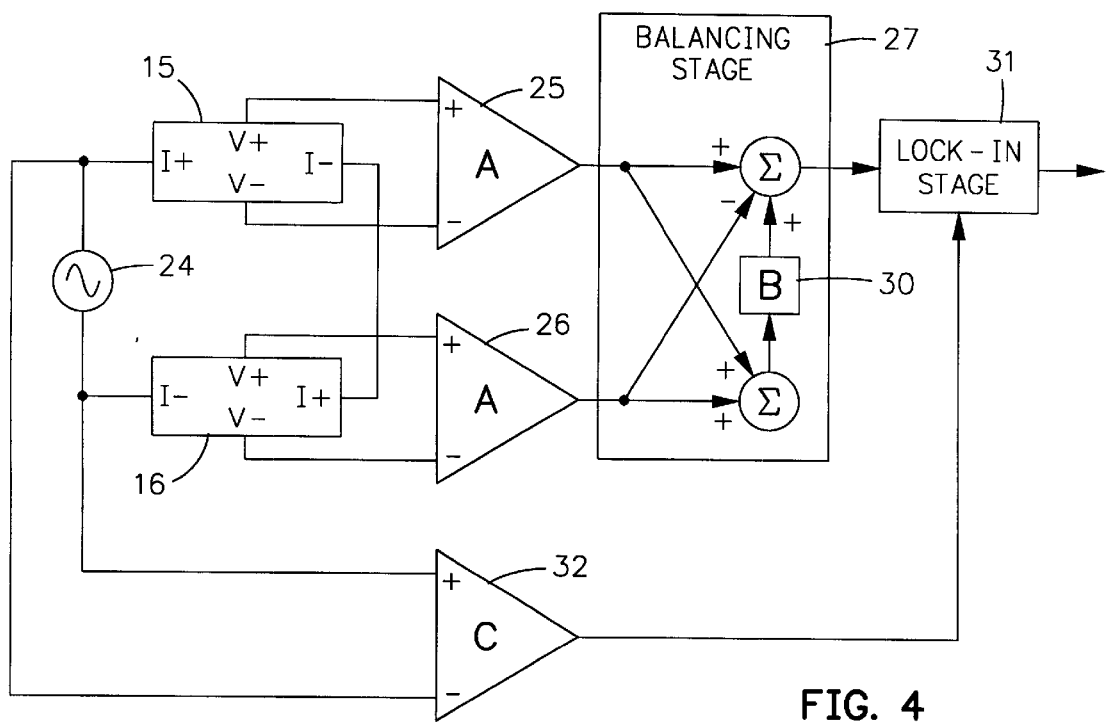
FIG. 4 is a block diagram of exemplary circuitry which would be employed with the FIG. 1 embodiment.

The circuit of FIG. 4 relates to the FIG. 1 embodiment. This preferred embodiment has the Hall sensor pair excited by a low frequency alternating current 24. The output voltage signals from the sensor pair are sensed in a high impedance manner by amplifiers 25 and 26. This circuitry then produces signals indicative of the sum and difference of the sensor signals in the pair. Further signal processing by balancing stage 27 is accomplished by adjusting the balance gain by means of element 30 to minimize the output signal of this stage in the absence of a magnetic sample in the proximity of the sensors. The resultant signal from the balancing stage is then used as the signal input to lock-in stage 31. A reference input to the lock-in stage is preferably synchronously coupled from excitation source 24 via signal amplifier 32. The output of the lock-in stage represents the amount of particle material present. A suitable output could be obtained in other ways without the synchronously coupled excitation source to the lock-in stage.

The lock-in stage is employed for signal processing by the lock-in technique. This technique is common and is also known as "phase sensitive detection," "mixing," and "heterodyning" in the art of signal processing. It is described as a signal processing stage having two inputs and an output. The technique entails exciting the measurement apparatus with an AC signal, and looking for an output signal synchronous to the alternating excitation. This technique serves to reject signal noise and interference present in the sensing apparatus. In the FIG. 4 embodiment, alternating excitation means 24 is the current used to excite the Hall sensors. A signal synchronous with the excitation signal is used as the "reference" input signal to the lock-in signal processing stage, as is commonly recognized in the art and as discussed above. The resultant difference signal from the sensors is configured as the other input to the lock-in stage. This difference signal may be optionally conditioned by the balancing stage mentioned above. In the case of the instrument described here, the output signal of the lock-in stage will be indicative of the amount of particle material 21 present. It is desirable to select the excitation frequency such that signal detection occurs in a region of frequency space where sensor noise and interference are minimized. It may also be desirable to detect at a frequency that is a multiple of the excitation frequency.

The actual implementation of the signal processing described above may in principle be accomplished by many available means, including active and passive analog electronics, digital signal processing, or a combination of these. The implementation may also include analog-to-digital or digital-to-analog conversion, or both.

Figure 3:
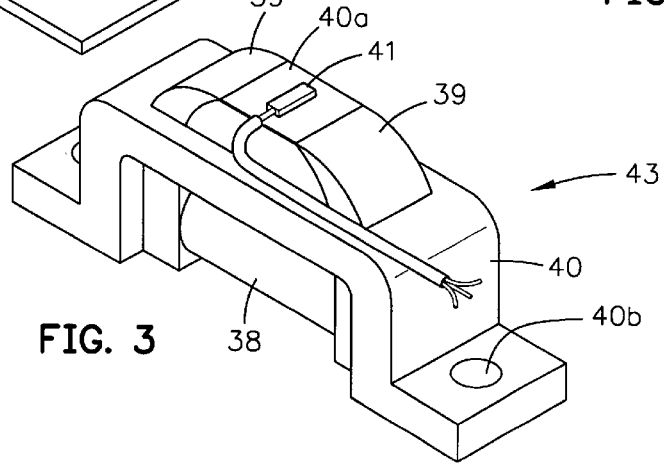
FIG. 3 is a perspective view of an alternative embodiment of the invention.

The requirement to pass the sample to be measured through a very narrow gap, as shown in the configuration of FIG. 1, may not be acceptable in some applications. For example, when the sample pattern has been deposited on a very thick substrate or even on the surface of some bulk material, it may be impossible to pass such a solid surface through a sufficiently small gap. For this type of application, the requisite DC magnetic field may be generated by a configuration such as shown in FIG. 3, in which sharply shaped iron "pole tips" generate a DC magnetic field from the back side of the Hall sensors. While this so-called "single sided" magnet design does allow the use of larger and bulk substrates, it has the disadvantage that the magnetic field at the position of the Hall sensors (and the sample) is non-uniform. This makes calibration of the instrument difficult, and can degrade the accuracy of the quantitative measurements to be made. For example, the non-uniform magnetic field will make the measurements strongly dependent on the separation between the sample and the sensors, so that small variations in the position of the sample will produce large uncertainties in the measurement. However, the output of the FIG. 3 apparatus can be useful in situations where the FIG. 1 embodiment cannot be used and a good estimate of the particle count is needed.

This measurement in the FIG. 3 apparatus is made by moving a well-defined pattern of magnetically susceptible particles 36 on substrate 37 into proximity of sensor 41 in the direction of arrow 42 and simultaneously in proximity to the magnetic field applied by means of permanent magnet structure 43. Magnet structure 43 is comprised of permanent magnet 38 and sharply shaped pole pieces 39, which are secured together by mounting device 40. The mounting device may be any non-conductive material such as plastic. In order to provide a surface on which to mount Hall sensor 41, the volume between pole pieces 39 and magnet 38 may be filed with plastic 40A. That may be a separate plastic element or it may be unitary with mounting device 40. Mounting device 40 is configured to be secured to a surface and holes 40B are provided to facilitate such attachment. The resulting signal, as a function of distance between the patterned particles and the sensor, compared with the signal when no sample particles are present, is indicative of the amount of particle material 36.

Figure 5:
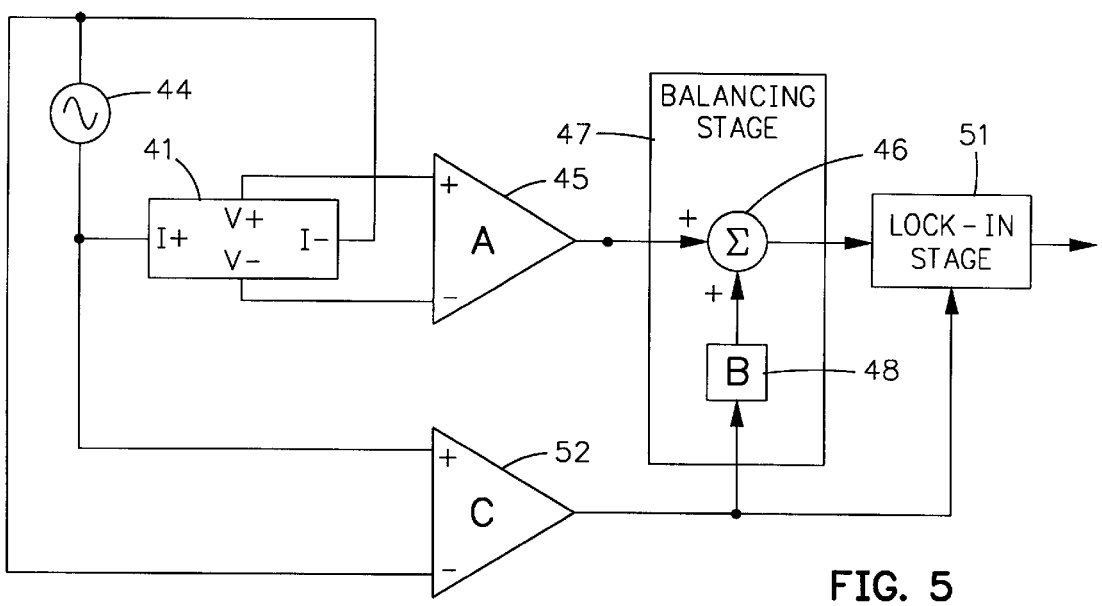
FIG. 5 is a block diagram of exemplary circuitry which could be employed with the FIG. 3 embodiment.

A circuit diagram for the embodiment of FIG. 3 is shown in FIG. 5. Here, Hall sensor 41 is excited by a low frequency alternating current 44. The output voltage signal from the sensor is sensed in a high impedance manner by amplifier 45. A signal proportional to the excitation is then summed at 46 with this signal indicative of the voltage across the sensor. Signal balancing occurs by adjusting the balancing gain in balancing stage 47 with balancing device 48 to minimize the output signal of this stage in the absence of a magnetic sample in the proximity of the sensors. The resulting sum signal is then detected by lock-in stage 51 using a reference signal synchronous to the excitation signal through amplifier 52 in the same manner as described in the preferred gradiometer embodiment above. The output of the lock-in stage represents the amount of particle material 36 present.

Figure 6:
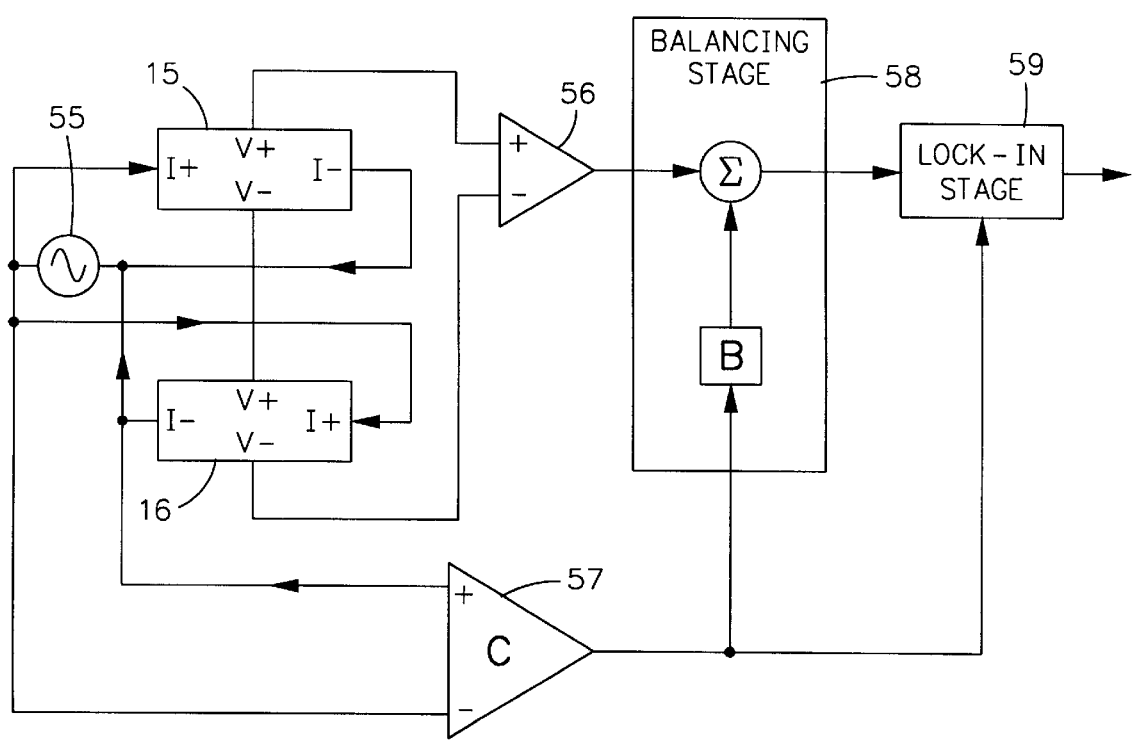
FIG. 6 is a block diagram incorporating an alternative manner of biasing the Hall sensors of FIG. 1.

With reference to FIG. 6 it can be appreciated that the invention contemplates two ways to bias the Hall sensors. In FIG. 4, Hall sensors 15, 16 are connected in series, so exactly the same bias current flows in both sensors. Since any variations in the bias current cause a change in the output voltage, any changes in one sensor will be exactly cancelled by the exact same change (of the opposite sign) in the other sensor. However, since there is also a significant voltage drop along the length of each of the Hall sensors, this also means that the voltage points labeled V+ on the two Hall sensors are at rather different voltage potentials. This prevents simply connecting the V− connection at the first sensor to the V+ connection of the second sensor. (Connecting these two points effectively produces a short-circuit current path for the bias current—from the V− point of the first sensor to the V+ point of the second sensor.) As shown in FIG. 4, this problem is avoided by using separate differential amplifiers 25, 26 attached to each of the Hall sensors. A large voltage difference between the two Hall sensors is also disadvantageous when using an AC bias current, because the voltage potentials at the voltage points on both sensors rapidly switch between fairly large potentials.

An alternative configuration is shown in FIG. 6 in which bias current 55 to the two Hall sensors 15, 16 is connected in parallel. This design is more susceptible to erroneous signals arising from variations in the bias current through one sensor, because such variations will not necessarily be exactly matched by a similar variation in the other sensor. However, in this design the voltage potentials at the V+ and V− points on the two sensors will all be at about the same voltage. Indeed, if the sensors were perfectly matched, in the absence of any magnetic field (such that the Hall voltage is zero) all four of the voltage taps on the two sensors would be at exactly the same voltage. Hence, in this configuration, the voltage taps of the two Hall sensors are connected together and a single differential amplifier 56 is used to detect the difference of the Hall voltages across the two sensors. Reference input through amplifier 57 and balancing stage 58 and lock-in stage 59 function in the same manner as previously described.

Either of these two configurations could be a preferred implementation, depending on the specific design of the rest of the measurement system. For example, the parallel bias scheme might be preferred when using AC current bias, thereby eliminating the large voltage swings when using an AC bias with the sensors wired in series. Conversely, the series bias scheme may be more desirable when using DC current bias. In any event, any combination of series/parallel and AC/DC can be used, depending on the features to be emphasized.

Figure 7:
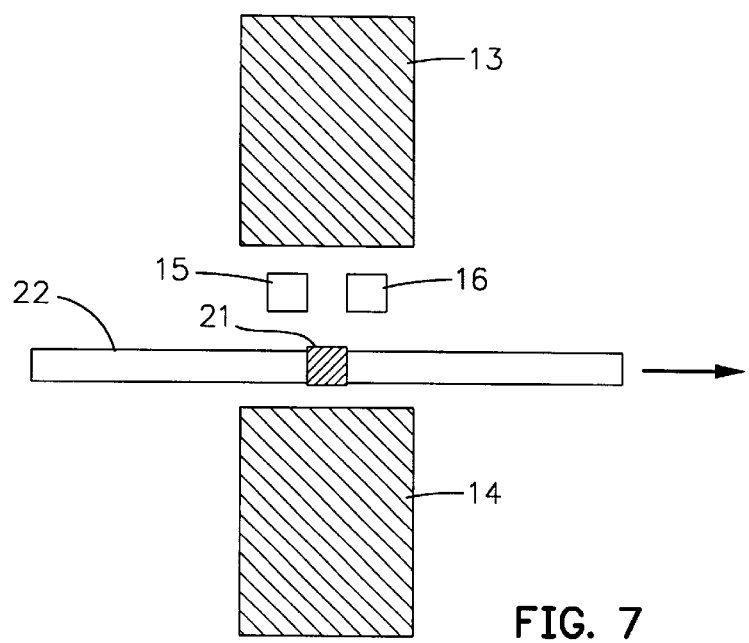
FIG. 7 is a schematic cross section showing the motion of the sample relative to the sensors of FIG. 1.
Figure 8:
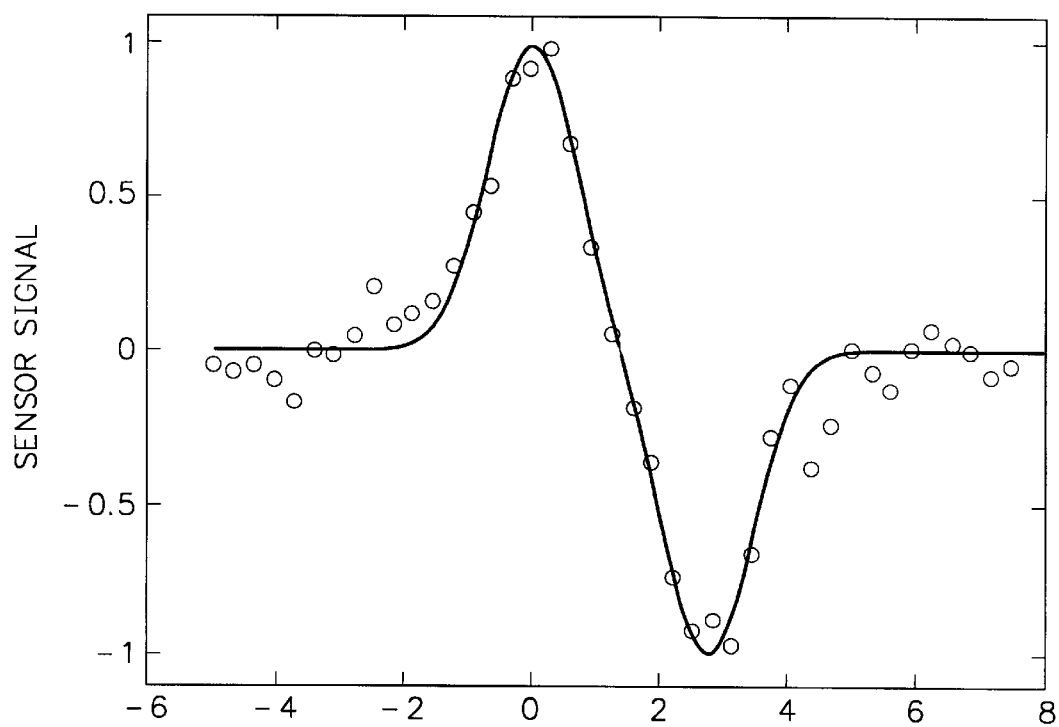
FIG. 8 is a plot of sensor outputs pursuant to the motion illustrated in FIG. 7.

With reference now to FIGS. 7 and 8, more details of the sensor response and relative motion of the sample and sensors are provided. In order to make the magnetic signal distinguishable from the background it is advantageous to move the sample relative to the sensor while recording the electronic sensor signal. This is illustrated in FIG. 7. As sample 21 moves over one or multiple sensors (15, 16) the magnetic flux of the sample will couple into the sensor. The sensor signal (FIG. 8), recorded as a function of position, reflects the geometry of the sample pattern and the spatial response of the sensor. If there are two sensors in a gradiometer configuration, as in FIG. 1, the sample will generate a signal of one polarity while close to one sensor, it will generate a signal of the opposite polarity while close to the other sensor.

FIG. 8 illustrates an ensemble of measurements plotted versus sample position. The solid curve represents a curve fit of an ideal response function using the method of least squares. It is clear that using both the position and signal voltage information, an absolute calculation of the magnetic moment of the sample can be derived. This is independent of the level of magnetic background and independent of any electronic or imbalance offsets in the signal voltage.

While the magnet pole pieces are preferably made of iron, the requirement is to have high magnetic permeability. They could be made of cobalt, nickel, or an appropriate alloy having the necessary characteristics. The pole pieces could be curved so that the gap, such as gap 12, is out front. Instead of the two magnets of FIG. 1, a single C-shaped magnet could be used. Substrate 22 could be a lateral flow membrane having region of interest 21. The substrate is preferably non-conductive and made of non-magnetic material, and could be made of plastic, wood, or other material satisfying these requirements. Substrate 22 can be moved by hand past the sensors, or the motion may be mechanized by using a stepper motor, a servo motor, or other means of generating motion by which the sample is moved relative to the sensors. The manner of motion is not critical to the invention.

The system of the invention has excellent sensitivity, in the range of 1 nanovolt to 10 microvolts. In other words, the invention is for a very sensitive magnetic sensor in the presence of large fields (500–1000 Oersted) to detect very small signals. The signals detected are changes in the magnetic field due to the presence of the target particles and the changes may be in the order of milli-Oersteds. The equation which is operative here is:

$$V = \frac{IB}{end}$$

Where V is the voltage change detected;
I is the bias current;
n is the carrier density;
B is the applied field;
d is the thickness of the sensing surface; and
e is the carrier charge.

In view of the above disclosure it is likely that modifications and improvements will occur to those skilled in this technical field which are within the scope of the invention as contemplated. Accordingly, the invention is to be limited only by the claims and equivalents thereto.

What is claimed is:

1. Apparatus for making quantitative measurements of agglutinations of magnetic particles comprising complexes of non-magnetized, magnetizable particles and target molecules, said apparatus comprising:
a substrate configured to receive samples of the agglutinations including unknown quantities of said magnetic particles in defined patterns thereon, the magnetizable particles in the samples being of known size and magnetic characteristics bound to the target molecules;
a magnet for providing a DC magnetic field, the magnetic field producing magnetization in the magnetizable particles when they are in the magnetic field;
at least one magnetic field sensing element in the magnetic field, said sensing element having an output signal conductor and producing an output signal when the samples are in operative relationship with said at least one sensing element; and,
a signal processor for converting said output signals from said at least one sensing element to provide a signal indicative of the quantity of the target molecules in a sample pattern.

2. The apparatus of claim 1, wherein said at least one sensing element comprises a Hall sensor with a bias excitation current flowing through said Hall sensor.

3. The apparatus of claim 1, wherein said at least one sensing element comprises a magneto-resistive sensor.

4. The apparatus of claim 1, wherein said at least one sensing element comprises two Hall sensors with a bias excitation current flowing through said sensors.

5. The apparatus of claim 1, wherein said at least one sensing element comprises two Hall sensors, each adapted to connect to a source of bias excitation current to be applied to said sensors.

6. The apparatus of claim 4, wherein the excitation current flows through said Hall sensors in series.

7. The apparatus of claim 4, wherein the excitation current flows through said Hall sensors in parallel.

8. The apparatus of claim 2, wherein the excitation current is an AC excitation current connected to said at least one Hall sensor.

9. The apparatus of claim 4, wherein the excitation current is an AC excitation current connected to said Hall sensors.

10. The apparatus of claim 1, and further comprising:
a code element on said substrate; and
a code reader mounted in position to read said code element when the samples are moved into operative relationship with said at least one sensing element.

11. The apparatus of claim 1, wherein said at least one sensing element senses the difference in the DC magnetic field caused by the presence of the samples.

12. The apparatus of claim 4, wherein said at least one sensing element senses the difference in the DC magnetic field caused by the presence of the samples.

13. The apparatus of claim 5, wherein said at least one sensing element senses the difference in the DC magnetic field caused by the presence of the samples.

14. The apparatus of claim 1, wherein said signal processor comprises:
an amplifier connected to the output of said at least one sensing element;
a balancing stage connected to said amplifier; and
a lock-in stage, the output of which is the signal indicative of the quantity of said target molecules in a sample pattern.

15. The apparatus of claim 4, wherein said signal processor comprises:
an amplifier connected to the output of said at least one sensing element;
a balancing stage connected to said amplifier;
a lock-in stage, the output of which is the signal indicative of the quantity of said target molecules in a sample pattern; and
means for synchronously coupling excitation current to said lock-in stage.

16. The apparatus of claim 5, wherein said signal processor comprises:
an amplifier connected to the output of said at least one sensing element;
a balancing stage connected to said amplifier;
a lock-in stage, the output of which is the signal indicative of the quantity of said target molecules in a sample pattern; and
means for synchronously the said lock-in stage to the sources of excitation current.

17. Apparatus for making quantitative measurements of agglutinations of magnetic particles comprising complexes of non-magnetized, magnetizable particles and target molecules, said apparatus comprising:
a substrate configured to receive samples of the agglutinations including unknown quantities of said magnetic particles in defined patterns thereon, the magnetizable particles in the samples being of known size and magnetic characteristics bound to the target molecules;
means for providing a DC magnetic field, the magnetic field producing magnetization in the magnetizable particles when they are in the magnetic field;
magnetic field sensing means in the magnetic field, said sensing means having output signal means and producing an output signal when the samples are in operative relationship with said sensing means; and,
means for converting said output signals from said sensing means to provide a signal indicative of the quantity of the target molecules in a sample pattern.

18. The apparatus of claim 17, and further comprising:
means for connecting said sensing means to a source of excitation current;
said sensing means comprises a Hall sensor connected to said means for connecting to the bias excitation current source.

19. The apparatus of claim 17, wherein said sensing means comprises a magneto-resistive sensor.

20. The apparatus of claim 17, wherein said sensing means comprises two Hall sensors, each adapted to connect to a source of bias excitation current to be applied to said sensors.

21. The apparatus of claim 20, wherein the excitation current flows through said Hall sensors in series.

22. The apparatus of claim 20, wherein the excitation current flows through said Hall sensors in parallel.

23. The apparatus of claim 18, wherein the excitation current is an AC excitation current.

24. The apparatus of claim 20, wherein the excitation current is an AC excitation current.

25. The apparatus of claim 17, and further comprising:
a code element on said substrate; and
a code reader mounted in position to read said code element when the samples are moved into operative relationship with said sensing means.

26. The apparatus of claim 17, wherein said converting means comprises a signal processor having:
    an amplifier connected to the output of said at least one sensing means;
    a balancing stage connected to said amplifier; and
    a lock-in stage, the output of which is the signal indicative of the quantity of the target molecules in said samples.

27. The apparatus of claim 20, wherein said converting means comprises a signal processor having:
    an amplifier connected to the output of said at least one sensing means;
    a balancing stage connected to said amplifier;
    a lock-in stage, the output of which is the signal indicative of the quantity of the target molecules in said samples in a pattern; and
    means for synchronously coupling excitation current to said lock-in stage.

28. A method for quantitatively determining target molecules in a sample pattern, said method comprising:
    applying at least one sample pattern having unknown quantities of target molecules in a predetermined configuration on a substrate, the sample pattern being comprised of non-magnetized, magnetizable particles of known size and magnetic characteristics coupled to the target molecules to form magnetic bound complex samples;
    providing a DC magnetic field;
    causing relative motion between the substrate and the magnetic field to place the sample pattern within the magnetic field;
    exciting the magnetizable particles in the pattern by means of the DC magnetic field to make them magnetic and thereby cause the magnetic particles to perturb the magnetic field;
    sensing the magnetic field changes caused by the presence of the magnetized particles in the magnetic field; and
    creating a signal representative of the quantity of target molecules in the field.

29. The method of claim 28, wherein said sensing is accomplished by means of at least one Hall sensor.

30. The method of claim 29, and further comprising applying an AC bias excitation current to the at least one Hall sensor.

31. The method of claim 28, and further comprising sensing the position of the substrate as the sample pattern is moved into the magnetic field.

32. The method of claim 28, wherein the magnetic field is created by means of a magnet.

33. The method of claim 28, wherein the signal representing the quantity of magnetic particles in the field is created by a signal processor.

34. The method of claim 33, and further comprising applying an AC bias excitation current to the at least one Hall sensor and to the signal processor.

35. The method of claim 28, wherein said sensing is accomplished by means of two Hall sensors connected in gradiometer configuration.

36. The method of claim 35, and further comprising applying an AC bias excitation current in series through the Hall sensors.

37. The method of claim 35, and further comprising applying an AC bias excitation current in parallel through the Hall sensors.

38. The method of claim 29, and further comprising determining the position of the substrate with respect to the at least one Hall sensor by means of a code element on the substrate and a code reader mounted in fixed relationship to the sensor.

39. The method of claim 28, wherein said sensing is accomplished by means of at least one magneto-resistive sensor.

40. The method of claim 39, and further comprising determining the position of the substrate with respect to the at least one magneto-resistive sensor by means of a code element on the substrate and a code reader mounted in fixed relationship to the sensor.

41. The apparatus of claim 1, wherein the DC magnetic field has a strength of 500–1,000 Oersted.

42. The apparatus of claim 41, wherein the said at least one sensing element is a Hall sensor.

43. The apparatus of claim 2, wherein the DC magnetic field has a strength of 500–1,000 Oersted.

44. The apparatus of claim 1, wherein the size of said sensing element is chosen to be about the same size as a sample pattern.

45. The apparatus of claim 2, wherein the size of said sensing element is chosen to be about the same size as a sample pattern.

46. The apparatus of claim 17, wherein the size of said sensing means is chosen to be about the same size as a sample pattern.

47. The apparatus of claim 18, wherein the size of said sensing means is chosen to be about the same size as a sample pattern.

48. The method recited in claim 28, wherein sensing is accomplished by a sensing element chosen to have a size about the same as the size of a sample pattern.

49. The apparatus of claim 29, wherein sensing is accomplished by a sensing element chosen to have a size about the same as the size of a sample pattern.

50. The apparatus of claim 17, wherein the DC magnetic field has a strength of 500–1,000 Oersted.

51. The apparatus of claim 18, wherein the DC magnetic field has a strength of 500–1,000 Oersted.

52. The method of claim 28, wherein the DC magnetic field has a strength of 500–1,000 Oersted.

53. The apparatus of claim 29, wherein the DC magnetic field has a strength of 500–1,000 Oersted.

* * * * *

UNITED STATES PATENT AND TRADEMARK OFFICE
CERTIFICATE OF CORRECTION

PATENT NO. : 6,518,747 B2
DATED : February 11, 2003
INVENTOR(S) : Ronald E. Sager et al.

It is certified that error appears in the above-identified patent and that said Letters Patent is hereby corrected as shown below:

Column 12,
Line 19, change "the," first occurance to -- coupling --

Signed and Sealed this

Twentieth Day of April, 2004

JON W. DUDAS
*Acting Director of the United States Patent and Trademark Office*